(12) United States Patent
Li et al.

(10) Patent No.: US 9,476,853 B2
(45) Date of Patent: Oct. 25, 2016

(54) SYSTEM AND METHOD FOR FORMING MICROWELLS

(71) Applicant: LIFE TECHNOLOGIES CORPORATION, Carlsbad, CA (US)

(72) Inventors: Shifeng Li, Fremont, CA (US); Jordan Owens, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 14/566,098

(22) Filed: Dec. 10, 2014

(65) Prior Publication Data

US 2015/0160153 A1 Jun. 11, 2015

Related U.S. Application Data

(60) Provisional application No. 61/914,263, filed on Dec. 10, 2013.

(51) Int. Cl.
*G01N 27/414* (2006.01)
*B01L 3/00* (2006.01)
*H01L 21/302* (2006.01)

(52) U.S. Cl.
CPC ..... *G01N 27/4145* (2013.01); *B01L 3/502707* (2013.01); *B01L 3/502761* (2013.01); *B01L 2200/0668* (2013.01); *B01L 2300/0636* (2013.01); *B01L 2300/0645* (2013.01); *B01L 2300/0877* (2013.01); *H01L 21/302* (2013.01)

(58) Field of Classification Search
CPC ............. G01N 27/4145; G01N 27/26; G01N 27/4148; H01L 21/302
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,800,159 A | 1/1989 | Mullis et al. | |
| 4,965,188 A | 10/1990 | Mullis et al. | |
| 5,112,456 A | 5/1992 | Worrell et al. | |
| 5,126,022 A | 6/1992 | Soane et al. | |
| 5,210,015 A | 5/1993 | Gelfand et al. | |
| 5,399,491 A | 3/1995 | Kacian et al. | |
| 5,498,392 A | 3/1996 | Wilding et al. | |
| 5,587,128 A | 12/1996 | Wilding et al. | |

(Continued)

FOREIGN PATENT DOCUMENTS

| | | |
|---|---|---|
| GB | 2461127 | 12/2009 |
| JP | 4262799 | 9/2004 |

(Continued)

OTHER PUBLICATIONS

Allen, Phillip E. et al., "CMOS Analog Circuit Design, Second Edition", *Oxford University Press*, 2002, 7 pages.

(Continued)

*Primary Examiner* — John C Ingham

(57) ABSTRACT

A method of forming a sensor component includes forming a first layer over a sensor pad of a sensor of a sensor array. The first layer includes a first inorganic material. The method further includes forming a second layer over the first layer. The second layer includes a polymeric material. The method also includes forming a third layer over the second layer, the third layer comprising a second inorganic material; patterning the third layer; and etching the second layer to define a well over the sensor pad of the sensor array.

10 Claims, 6 Drawing Sheets

(56) References Cited

U.S. PATENT DOCUMENTS

| | | | |
|---|---|---|---|
| 5,854,033 A | 12/1998 | Lizardi | |
| 5,858,195 A | 1/1999 | Ramsey | |
| 6,001,229 A | 12/1999 | Ramsey | |
| 6,010,607 A | 1/2000 | Ramsey | |
| 6,033,546 A | 3/2000 | Ramsey | |
| 6,051,422 A * | 4/2000 | Kovacs | C12M 41/46 204/403.06 |
| 6,054,034 A | 4/2000 | Soane et al. | |
| 6,174,670 B1 | 1/2001 | Wittwer et al. | |
| 6,399,952 B1 | 6/2002 | Maher et al. | |
| 6,613,525 B2 | 9/2003 | Nelson et al. | |
| 6,960,437 B2 | 11/2005 | Enzelberger et al. | |
| 7,049,645 B2 | 5/2006 | Sawada et al. | |
| 7,190,026 B2 | 3/2007 | Lotfi | |
| 7,462,512 B2 | 12/2008 | Levon et al. | |
| 7,535,232 B2 | 5/2009 | Barbaro et al. | |
| 9,228,974 B2 * | 1/2016 | Chang | G01N 27/4145 |
| 2006/0147983 A1 | 7/2006 | O'uchi, et al. | |
| 2007/0059741 A1 | 3/2007 | Kamahori et al. | |
| 2007/0207471 A1 | 9/2007 | Osaka et al. | |
| 2008/0166727 A1 | 7/2008 | Esfandyarpour et al. | |
| 2008/0286762 A1 | 11/2008 | Miyahara et al. | |
| 2008/0286767 A1 | 11/2008 | Miyahara et al. | |
| 2009/0127589 A1 | 5/2009 | Rothberg et al. | |
| 2010/0052080 A1 * | 3/2010 | Garcia Tello | G01N 27/3278 257/414 |
| 2010/0137143 A1 | 6/2010 | Rothberg et al. | |
| 2010/0300895 A1 * | 12/2010 | Nobile | G01N 27/4145 205/775 |
| 2012/0000274 A1 * | 1/2012 | Fife | G01N 27/4148 73/61.41 |
| 2012/0001235 A1 | 1/2012 | Fife | |
| 2012/0045368 A1 * | 2/2012 | Hinz | G01N 27/4148 422/69 |
| 2012/0292770 A1 * | 11/2012 | Wang | B81B 7/0025 257/753 |
| 2013/0189790 A1 | 7/2013 | Li et al. | |

FOREIGN PATENT DOCUMENTS

| | | |
|---|---|---|
| WO | 99/19717 | 4/1999 |
| WO | 02/24322 | 3/2002 |
| WO | 2010/020675 | 2/2010 |
| WO | 2013/109559 | 7/2013 |

OTHER PUBLICATIONS

Anderson, E. et al., "A system for multiplexed direct electrical detection of DNA synthesis", *Sensors and Actuators B Chem.*, vol. 129, 2008, 79-86.

Baker, R J. , "CMOS Circuit Design, Layout, and Simulation", *Wiley IEEE Press*, 2008.

Barbaro, M. et al., "Fully electronic DNA hybridization detection by a standard CMOS biochip", *Sensors and Actuators B Chemical*, vol. 118, 2006, 41-46.

Bard, Allen et al., "Electrochemical Methods: Fundamentals and Applications", *Wiley*, 2001.

Cao, Guozhong , "Nanostructures & Nanomaterials: Synthesis, Properties & Applications", *Imperial College Press*, 2004.

Dieffenbach, Carl (Ed) et al., "PCR Primer: A Laboratory Manual, Second Edition", *Cold Spring Harbor Laboratory Press*, 2003.

Doering, Robert (Ed) et al., "Handbook of Semiconductor Manufacturing Technology, Second Edition", *CRC Press*, 2007.

Elwenspoek, M et al., "Silicon Micromachining", *Cambridge University Press*, (2004 edition is paperback version of 1998 hardcover edition), 2004.

Hammond, P. et al., "Design of a Single-Chip pH Sensor Using a Conventional 0.6-μm CMOS Process", *IEEE Sensors Journal*, vol. 4(6), 2004, 706-712.

Heer, F et al., "Single-chip microelectronic system to interface with living cells", *Biosensors and Bioelectronics*, vol. 22, 2007, 2546-2553.

Hizawa, T et al., "Fabrication of a two-dimensional pH image sensor using a charge transfer technique", *Sensors and Actuators B Chemical*, vol. 117, 2006, 509-515.

Hughes, R C. et al., "Chemical Microsensors", *Science*, vol. 254, 1991, 74-80.

Krause, M. et al., "Extended gate electrode arrays for extracellular signal recordings", *Sensors and Actuators B*, vol. 70, 2000, pp. 101-107.

Levinson, Harry , "Principles of Lithography, Second Edition", *SPIE Press Monograph* vol. PM146, 2005.

Martinoia, S. et al., "Development of ISFET Array-Based Microsystems for Bioelectrochemical measurements of cell populations", *Biosensors & Bioelectronics*, vol. 16, 2001, pp. 1043-1050.

Milgrew, M. et al., "A large transistor based sensor array chip for direct extracellular imaging", *Sensors and Actuators B Chemical*, vol. 111-112, 2005, 347-353.

Milgrew, M. et al., "The development of scalable sensor arrays using standard CMOS technology", *Sensors and Actuators B*, vol. 103, 2004, 37-42.

Mir, Monica et al., "Integrated electrochemical DNA biosensors for lab-on-a-chip devices", *Electrophoresis*, vol. 30, 2009, 3386-3397.

Ohmori, Kazuyuki et al., "Performance of Cu Dual-Damascene Interconnects Using a Thin Ti-Based Self-Formed Barrier Layer for 28nm Node and Beyond", *Japanese Journal of Applied Physics*, vol. 49(05FD01), 2010, 1-4.

Saliterman, Steven , "Fundamentals of BioMEMS and Medical Microdevices", *SPIE Press*, Wiley-Interscience, 2006.

Sawyer, Donald T. et al., "Electrochemistry for Chemists, Second Edition", *Wiley-Interscience*, 1995.

Sia, S et al., "Microfluidic devices fabricated in poly(dimethylsiloxane) for biological studies", *Electrophoresis*, 24:, 2003, 3563-3576.

Trojanowicz, Marek , "Recent developments in electrochemical flow detections—A review Part I. Flow analysis and capillary electrophoresis", *Analytica Chimica Acta*, vol. 653, 2009, 36-58.

Unger, M et al., "Monolithic Microfabricated Valves and Pumps by Multilayer Soft Lithography", *Science*, 288:, 2000, 113-116.

Veendrick, Harry , "Deep-Submicron CMOS ICs: From Basics to ASICs", *Kluwer Academic Publishing*, 1998.

Xu, Xiaoli et al., "Integration of electrochemistry in micro-total analysis systems for biochemical assays: Recent developements", *Talanta*, vol. 80, 2009, 8-18.

Yeow, T.C.W. et al., "A very large integrated pH-ISFET sensor array chip compatible with standard CMOS processes", *Sensor and Actuators B*, vol. 44, 1997, 434-440.

* cited by examiner

SYSTEM AND METHOD FOR FORMING MICROWELLS

CROSS-REFERENCE TO RELATED APPLICATION(S)

This application claims benefit of U.S. Provisional Application No. 61/914,263, filed Dec. 10, 2013, which is incorporated herein by reference in its entirety.

FIELD OF THE DISCLOSURE

This disclosure, in general, relates to systems and methods for forming microwells.

BACKGROUND

Electronic sensor arrays are finding increased use for detecting analytes in fluids, such as gases or liquids. In particular, arrays of sensors based on field effect transistors are finding use in detecting ionic components, such as various cations, anions, or pH. Such sensors are often referred to as ion-sensitive field effect transistors (ISFETs).

Recently, such sensor arrays have found use in sequencing polynucleotides. Nucleotide addition results in the release of ionic species that influence the pH of a local environment. Sensors of the sensor arrays are used to detect changes in pH resulting from the nucleotide addition in the local environment. However, the pH of the local environment can be influenced by adjacent environments, referred to as crosstalk, and can be influenced by the interaction of various materials with hydrogen ions, referred to as buffering, leading to lower accuracy and less sensitivity to the changes caused by nucleotide addition.

As such, an improved sensor array would be desirable.

SUMMARY

In a first aspect, a method of forming a sensor component includes forming a first layer over a sensor pad of a sensor of a sensor array. The first layer includes a first inorganic material. The method further includes forming a second layer over the first layer. The second layer includes a polymeric material. The method also includes forming a third layer over the second layer, the third layer comprising a second inorganic material; patterning the third layer; and etching the second layer to define a well over the sensor pad of the sensor array.

In a second aspect, an apparatus includes an array of sensors. A sensor of the array of sensors includes a sensor pad. The apparatus further includes a first insulative layer disposed over the array of sensors and defining an access exposing the sensor pad through the first insulative layer. The first insulative layer includes an inorganic material. The apparatus can further include a second insulative layer disposed over the first insulative layer and defining a well in fluid communication with the access and exposing the sensor pad, the second insulative layer comprising a polymeric material.

In a third aspect, a method of forming a sensor component includes forming a first layer over a sensor pad of a sensor of a sensor array, the first layer comprising a first inorganic material; forming a second layer over the first layer, the second layer comprising a polymeric material; forming a third layer over the second layer, the third layer comprising a second inorganic material; patterning the third layer; etching the second layer to define a well over the first layer and the sensor pad of the sensor array; and etching to form an access through the first layer and to remove the third layer, the access exposing the sensor pad to the well.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

In an exemplary embodiment, an array of sensors includes sensors having sensor pads. A first insulative layer is disposed over the array of sensors and provides access exposing the sensor pads. A second insulative layer is disposed over the first insulative layer and defines a well, providing fluid communication between a bulk fluid and the access exposing the sensor pads. Optionally, a third insulative layer is disposed over the first and second insulative layers and provides access for fluid communication with the well and the access. In an example, the first insulative layer can include an oxide or a nitride of silicon. In another example, the second insulative layer includes a polymeric material. For example, the second insulative layer includes polyimide. The optional third insulative layer can include an oxide or a nitride of silicon.

In another exemplary embodiment, a method of forming a sensor component includes forming a first insulative layer over an array of sensors, forming a second insulative layer over the first insulative layer and optionally forming a third insulative layer over the second insulative layer. The second insulative layer can include a polymeric material, such as a polyimide material. The method further includes patterning the third insulative layer and etching the second insulative layer using the third insulative layer as a mask to define a well over the sensor pad of the sensor array. The first insulative layer can be patterned prior to depositing the second insulative layer. Alternatively, the first insulative layer can be patterned after etching to define a well within the second insulative layer. In an example, the third insulative layer includes an oxide of silicon, such as a low temperature oxide of silicon. The first insulative layer can include an oxide or a nitride of silicon.

Figure 1:
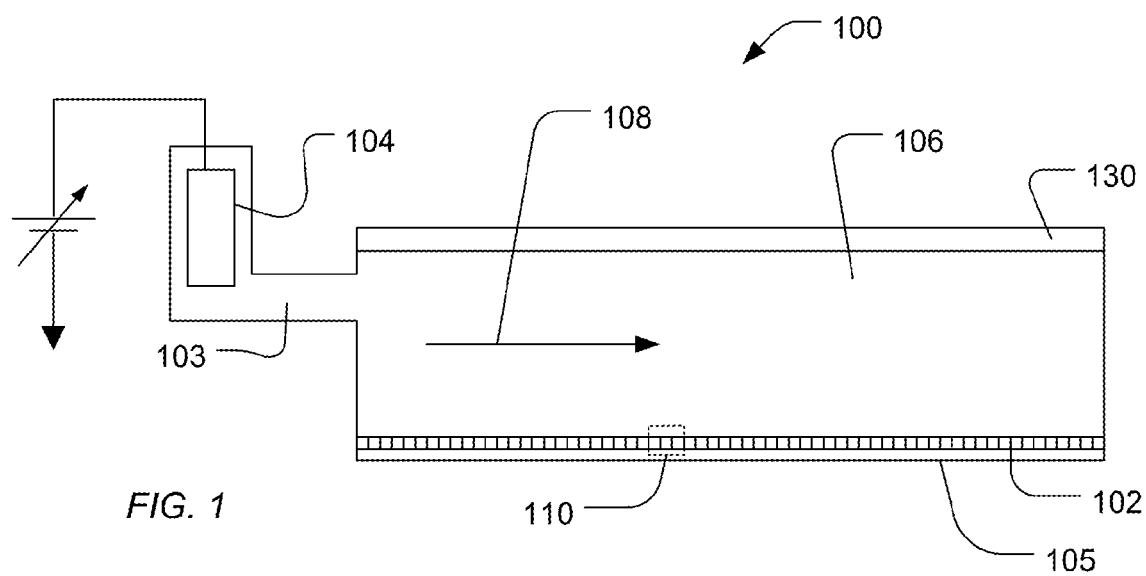
FIG. 1 includes an illustration of an exemplary sensing device.

In a particular embodiment, a sequencing system includes a flow cell in which a sensory array is disposed, includes communication circuitry in electronic communication with the sensory array, and includes containers and fluid controls in fluidic communication with the flow cell. In an example, FIG. 1 illustrates an expanded and cross-sectional view of a flow cell 100 and illustrates a portion of a flow chamber 106. A reagent flow 108 flows across a surface of a microwell array 102, in which the reagent flow 108 flows over the open ends of microwells of the microwell array 102. The microwell array 102 and a sensor array 105 together can form an integrated unit forming a lower wall (or floor) of flow cell 100. A reference electrode 104 can be fluidly coupled to flow chamber 106. Further, a flow cell cover 130 encapsulates flow chamber 106 to contain reagent flow 108 within a confined region.

Figure 2:
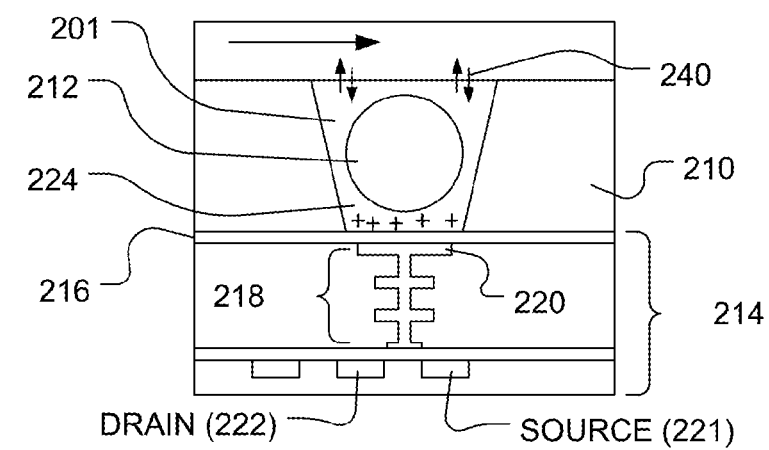
FIG. 2 includes an illustration of an exemplary microwell and associated sensor.

FIG. 2 illustrates an expanded view of a microwell 201 and a sensor 214, as illustrated at 110 of FIG. 1. The volume, shape, aspect ratio (such as base width-to-well depth ratio), and other dimensional characteristics of the microwells can be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 optionally separated from the microwell interior by a passivation layer 216. The sensor 214 can be responsive to (and generate an output signal related to) the amount of a charge 224 present on passivation layer 216 opposite the sensor plate 220 or on the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, wash solutions, and other reagents can move in and out of the microwells by a diffusion mechanism 240.

In an embodiment, reactions carried out in the microwell 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, then multiple copies of the same analyte can be analyzed in the microwell 201 at the same time in order to increase the output signal generated. In an embodiment, multiple copies of an analyte can be attached to a solid phase support 212, either before or after deposition into the microwell 201. The solid phase support 212 can be microparticles, nanoparticles, beads, solid or porous support comprising gels, or the like. For simplicity and ease of explanation, solid phase support 212 is also referred herein as a particle. For a nucleic acid analyte, multiple, connected copies can be made by rolling circle amplification (RCA), exponential RCA, or like techniques, to produce an amplicon without the need of a solid support.

Figure 3:
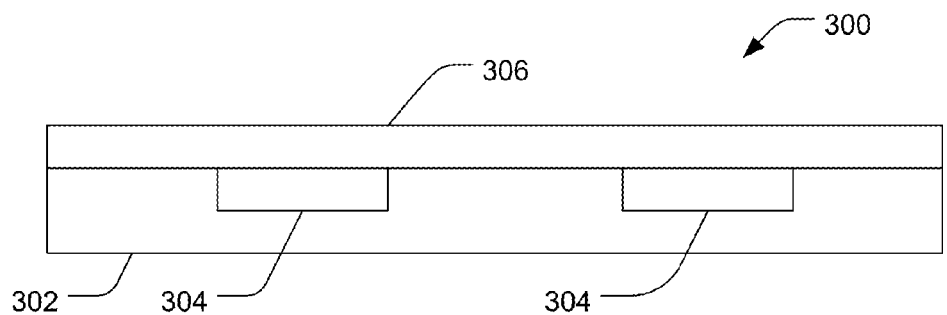
FIG. 3, FIG. 4, FIG. 5, FIG. 6, FIG. 7, FIG. 8, FIG. 9, FIG. 10, and FIG. 11 include illustrations of exemplary workpieces during a process for forming microwells.

In an example, FIG. 3 illustrates a workpiece in which a substrate 302 includes sensor pads 304. While not illustrated, the substrate 302 can include further functional layers forming sensors attached to the sensor pads 304. In particular, the sensor pads 304 are exposed at a surface of the substrate 302. Sensor pads 304 can be formed of various materials including gold, silver, copper, aluminum, titanium, titanium nitride, titanium, oxides of tantalum, aluminum, or hafnium, or a combination thereof.

As illustrated in FIG. 3, a first insulative material 306 is deposited over the substrate 302 and the sensor pads 304. Optionally, the first insulative material 306 can be deposited between the sensor pads 304. The first insulative layer 306 can be formed of an inorganic material, such as a ceramic material. For example, the ceramic material can include an oxide or a nitride of silicon.

Figure 4:
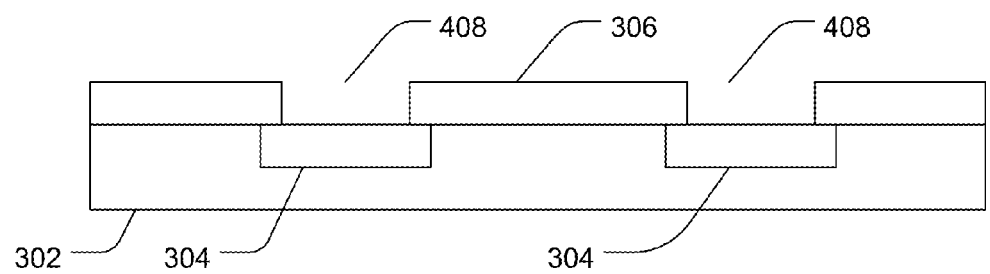

The first insulative layer 306 can be patterned to form openings or accesses 408 exposing the sensor pads 304, as illustrated in FIG. 4. The openings or accesses 408 can be defined by patterning the first insulative layer 306, using photolithography followed by etching. For example, the first insulative layer can be etched using a wet etch process. In another example, the first insulative layer 306 can be patterned using a plasma etch, such as a fluorinated plasma etch. While the insulative layer 306 is illustrated as partially residing over the sensor pads 304, alternatively, the sensor pads 304 may not be obstructed by the first insulative layer 306 or the first insulative layer 306 can reside at least partially between the sensor pads 304.

Figure 5:
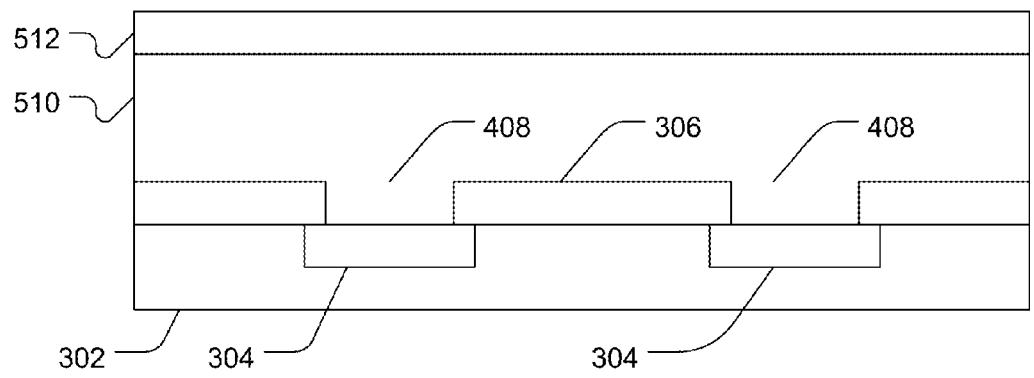

As illustrated in FIG. 5, a second insulative layer 510 can be deposited over the first insulative layer 306 and into the openings or accesses 408. In particular, the second insulative layer 510 is formed of a polymeric material. For example, polymeric material can include polyimide, polynorbornenes, benzocyclobutene, fluorinated polymers, epoxies, other photoresist materials, or any combination thereof. In an example, the fluorinated polymer includes fluorinated oxolane polymer. In another example, the polyimide material can be an aromatic polyimide, such as the product of a dianhydride and a diamine, at least one of which including a homogeneous or heterogeneous cyclic structure. Exemplary aromatic dianhydrides include PMDA, DSDA, BTDA, BPDA, ODPA, HQDA, BPADA, or any combination thereof. Exemplary diamines can include meta, ortho, or para phenylene diamine, oxydianiline, other aromatic ether diamines, dimethylacetamide, or any combination thereof. For example, the polyimide can be formed from reactants such as N, N,-dimethylacetamide and methylpyrrolidinone. In another example, the polyimide can be formed of reactants such as pyromellitic dianhydride (PMDA) and 4,4'-oxydianiline (ODA).

In addition, a further third insulative layer 512 can be deposited over the second insulative layer 510. The third insulative layer 512 can be formed of an inorganic material, such as a ceramic material. In particular, the third insulative layer 512 can be formed of an oxide or a nitride of silicon. In an example, the oxide of silicon can be a low temperature oxide of silicon. A low temperature oxide of silicon is an oxide of silicon formed at a temperature in a range of 100° C. to 650° C., such as a range of 100° C. to 450° C. The low temperature oxide of silicon can be derived from tetraethoxy orthosilicate (TEOS), depleted silane, or bis-diethylaminosilane, among other silane species. For example, the oxide of silicon can be deposited by atomic layer deposition (ALD).

Figure 6:
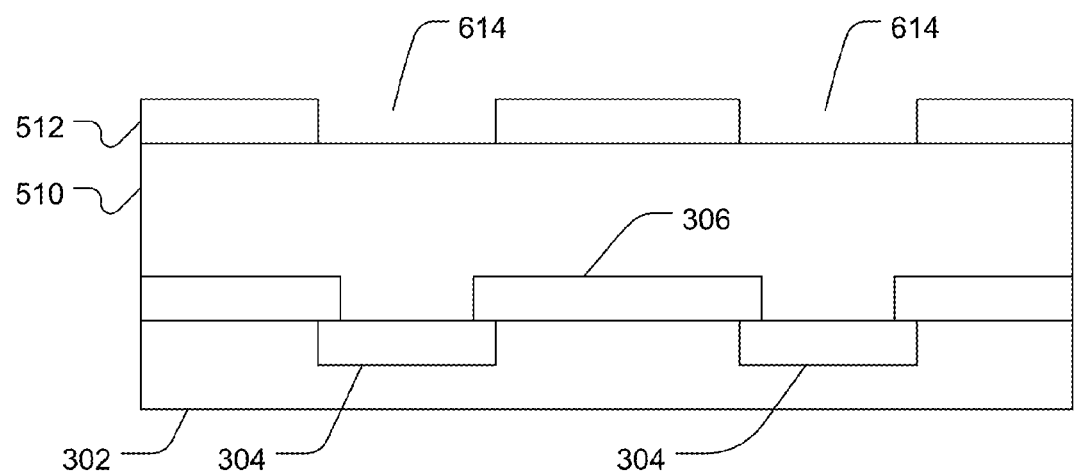

As illustrated in FIG. 6, the third insulative layer 512 can be etched to define mask openings 614. In particular, the third insulative layer 512 can be patterned using photolithography followed by etching. In an example, a wet etch can be used. In another example, a plasma etch can be used, such as a fluorinated plasma etch.

Figure 7:
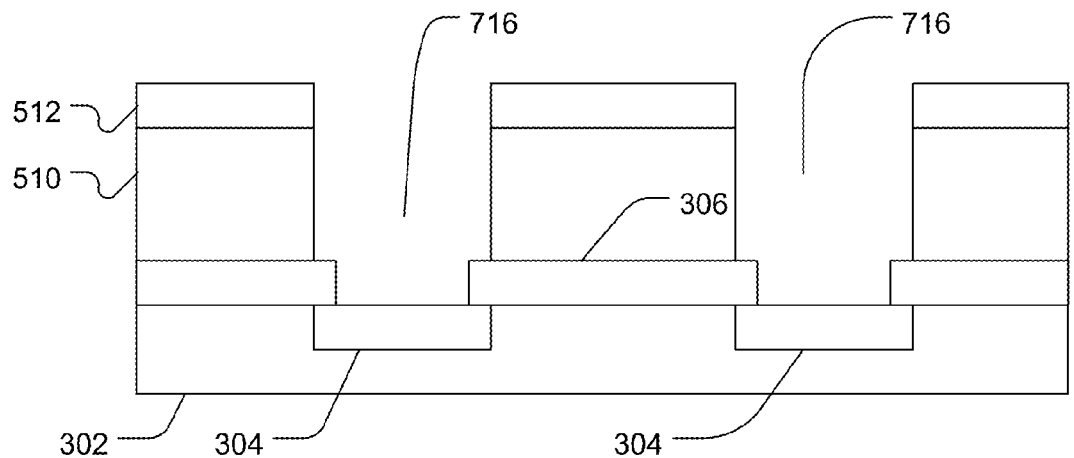

Using the patterned third insulative layer 512 as a mask, the second insulative layer 510 can be patterned to define wells 716, as illustrated in FIG. 7. For example, the second insulative layer 510 can be patterned using an etch process. For example, the second insulative layer 510 can include a positive photoresist material patterned using the third insulative layer 512 as a mask. The second insulative layer 510 can then be developed, providing wells 716. As a result, the polymeric material of the second insulative layer 510 forms a well and is removed from the openings or accesses 408 to provide fluidic access to the sensor pads 304. In another example, the second insulative layer 510 can be etched using a wet etch or using a plasma etch, such as an oxygen-containing plasma.

Figure 8:
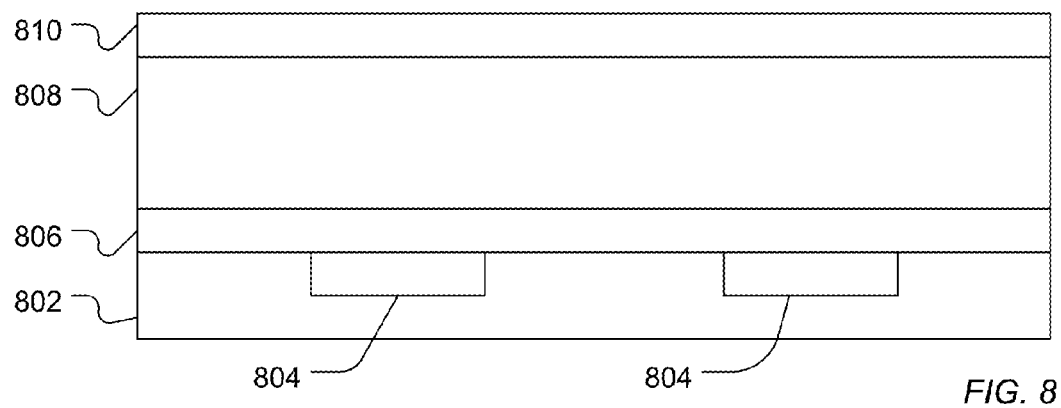

In an alternative example illustrated in FIG. 8, a substrate 802 includes sensor pads 804 disposed at a surface of substrate 802. Further functional layers can be formed in the substrate 802 to define sensor devices in electrical communication with the sensor pads 804.

A first insulative layer 806 can be deposited over the substrate 802 including the sensor pads 804. The first insulative layer 806 can be formed of an inorganic material, such as a ceramic material. In particular, the ceramic material can be an oxide or a nitride of silicon. In particular, the material of the first insulative layer 806 is an oxide of silicon.

In addition, a second insulative layer 808 can be deposited over the first insulative layer 806. In an example, the second material layer 808 includes a polymeric material. For example, the polymeric material can include a polymer as described above. In particular, the polymeric material is a polyimide material selected from the polyimides described above.

In addition, a third insulative layer 810 can be deposited over the second insulative layer 808, as illustrated in FIG. 8. The third insulative material layer 810 can include an inorganic material, such as a ceramic material. In an example, ceramic material includes an oxide or a nitride of silicon. In a further example, the ceramic material includes an oxide of silicon. In particular, the third insulative layer 810 is a low temperature oxide of silicon. For example, the third insulative layer 810 can be deposited using a low temperature atomic layer deposition technique.

Figure 9:
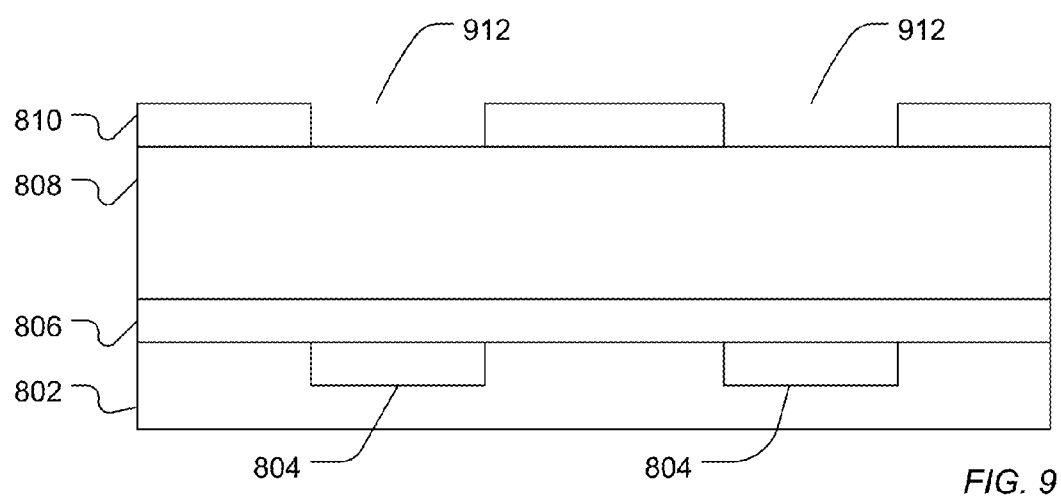

As illustrated in FIG. 9, the third insulative layer 810 can be patterned to define mask openings 912. For example, the third insulative layer 810 can be patterned by applying a photolithographic mask over the layer 810 followed by etching the layer 810. For example, a plasma etch, such as a plasma etch using a fluorinated plasma, can be used to define the openings 912 of the layer 810. In another example, a wet etch method can be used.

Figure 10:
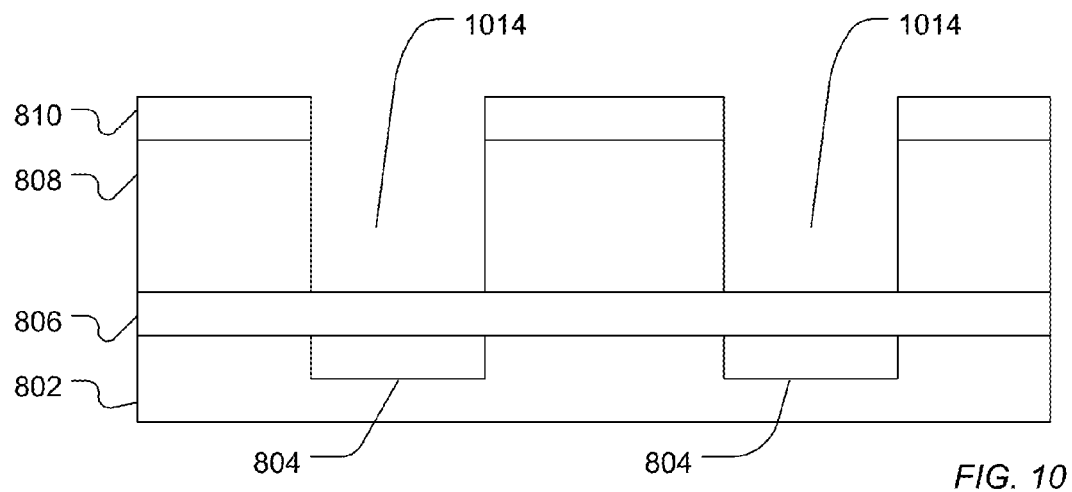

As illustrated in FIG. 10, the second insulative layer 808 can be etched to define wells 1014. For example, the second material layer 808 can be etched using a plasma etch, such as an oxygen-containing plasma. In another example, the second material layer 808 can be etched using a wet etch process. In a particular example, when the second insulative layer 808 is formed of a positive photoresist material, the second insulative layer 808 can be patterned using electromagnetic radiation such as e-beam, ultraviolet light or infrared light, using the third insulative layer 810 as a mask. Subsequently, the second insulative layer 808 can be etched using a wet etch to remove developed material.

Figure 11:
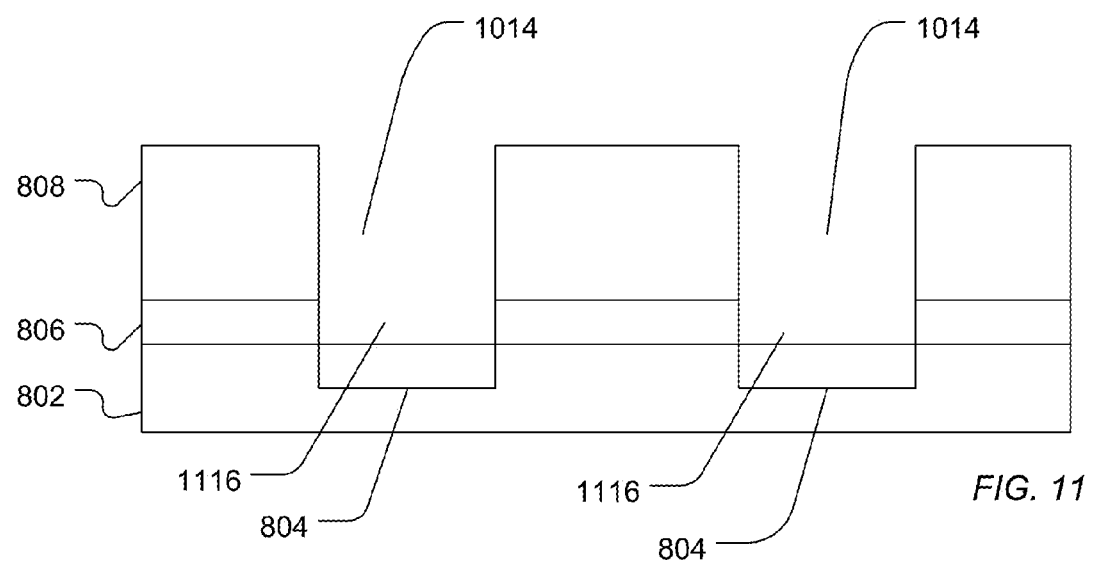

Following the patterning of the second insulative layer 808, the first insulative layer 806 can be patterned to define an access or opening 1116 to the sensor pads 804. In an example, the first insulative layer 806 can be patterned using a wet etch process. In another example, the first insulative layer 806 can be patterned using a plasma etch process, such as a fluorinated plasma etch process. In particular, while etching the first insulative layer 806, at least portion of the third insulative layer 810 can be removed. While FIG. 11 illustrates the third insulative layer 810 as being completely removed, portions or residue of the material of the third insulative layer 810 can remain over the second insulative layer 808.

Such a method of forming wells over sensor pads advantageously provides a low buffering surface, while preventing the formation of cavities in proximity to the sensor pads. As such, the resulting sensor including the wells have low buffering, higher signal-to-noise ratios, and can have a reduced carry forward error during readings.

Figure 12:
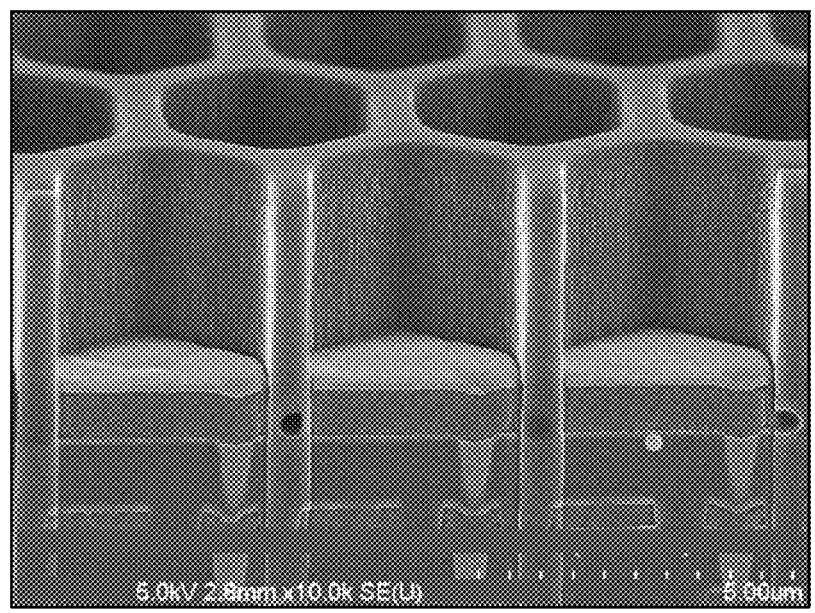
FIG. 12 and FIG. 13 include SEM images of exemplary microwells.
Figure 13:
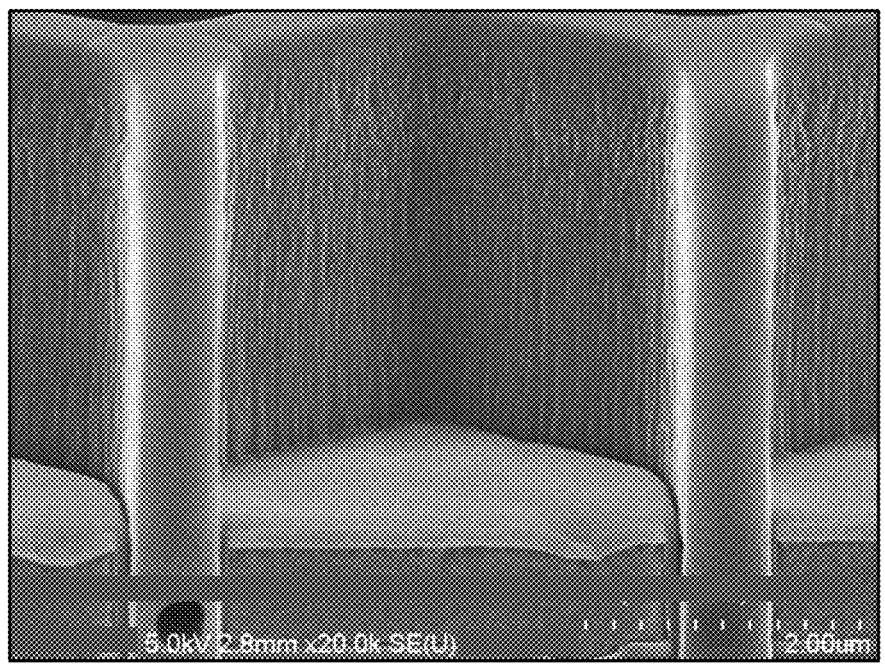

In an example, FIG. 12 and FIG. 13 include SEM images of exemplary well structures that include a low temperature oxide over a polyimide sidewall structure. The resulting wells define near vertical walls and correspond well to underlying sensor circuitry.

In a first aspect, a method of forming a sensor component includes forming a first layer over a sensor pad of a sensor of a sensor array. The first layer includes a first inorganic material. The method further includes forming a second layer over the first layer. The second layer includes a polymeric material. The method also includes forming a third layer over the second layer, the third layer comprising a second inorganic material; patterning the third layer; and etching the second layer to define a well over the sensor pad of the sensor array.

In an example of the first aspect, the first inorganic material comprises an oxide of silicon.

In another example of the first aspect and the above examples, the polymeric material comprises a polyimide.

In a further example of the first aspect and the above examples, the second inorganic material comprises a low temperature oxide of silicon.

In an additional example of the first aspect and the above examples, the method further includes patterning the first layer. For example, patterning the first layer comprises patterning the first layer prior to forming the second layer. In another example, patterning the first layer comprises patterning the first layer after etching the second layer. In an additional example, patterning the first layer includes etching with a fluorine-containing plasma.

In a second aspect, an apparatus includes an array of sensors. A sensor of the array of sensors includes a sensor pad. The apparatus further includes a first insulative layer disposed over the array of sensors and defining an access exposing the sensor pad through the first insulative layer. The first insulative layer includes an inorganic material. The apparatus can further include a second insulative layer disposed over the first insulative layer and defining a well in fluid communication with the access and exposing the sensor pad, the second insulative layer comprising a polymeric material.

In an example of the second aspect, the method further includes a third insulative layer disposed over the second insulative layer and defining an access in fluid communication with the well through the third insulative layer, the third insulative layer comprising a second inorganic material. For example, the second inorganic material includes a low temperature oxide of silicon.

In another example of the second aspect and the above examples, the polymeric material includes polyimide.

In a further example of the second aspect and the above examples, the inorganic material includes an oxide of silicon.

In an additional example of the second aspect and the above examples, the sensor is a chemical field effect transistor (chemFET).

In another example of the second aspect and the above examples, the sensor pad is coupled to a floating gate.

In a third aspect, a method of forming a sensor component includes forming a first layer over a sensor pad of a sensor of a sensor array, the first layer comprising a first inorganic material; forming a second layer over the first layer, the second layer comprising a polymeric material; forming a third layer over the second layer, the third layer comprising a second inorganic material; patterning the third layer; etching the second layer to define a well over the first layer and the sensor pad of the sensor array; and etching to form an access through the first layer and to remove the third layer, the access exposing the sensor pad to the well.

In an example of the third aspect, the first inorganic material comprises an oxide of silicon.

In another example of the third aspect and the above examples, the polymeric material comprises a polyimide.

In a further example of the third aspect and the above examples, the second inorganic material comprises a low temperature oxide of silicon.

In an additional example of the third aspect and the above examples, etching to form the access includes etching with a fluorine-containing plasma.

As used herein, the terms "over" or "overlie" refers to a position away from a surface relative to a normal direction from the surface. The terms "over" or "overlie" are intended to permit intervening layers or direct contact with an underlying layer. As described above, layers that are disposed over or overlie another layer can be in direct contact with the identified layer or can include intervening layers.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and FIG.s are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of forming a sensor component, the method comprising:
   forming a first layer over a sensor pad of a sensor of a sensor array, the first layer comprising a first inorganic material;
   forming a second layer over the first layer, the second layer comprising a polymeric material;
   forming a third layer over the second layer, the third layer comprising a second inorganic material;
   patterning the third layer;
   etching the second layer to define a well over the sensor pad of the sensor array; and
   patterning the first layer after etching the second layer.

2. The method of claim 1, wherein the first inorganic material comprises an oxide of silicon.

3. The method of claim 1, wherein the polymeric material comprises a polyimide.

4. The method of claim 1, wherein the second inorganic material comprises a low temperature oxide of silicon.

5. The method of claim 1, wherein patterning the first layer includes etching with a fluorine-containing plasma.

6. A method of forming a sensor component, the method comprising:
   forming a first layer over a sensor pad of a sensor of a sensor array, the first layer comprising a first inorganic material;
   forming a second layer over the first layer, the second layer comprising a polymeric material;
   forming a third layer over the second layer, the third layer comprising a second inorganic material;
   patterning the third layer;
   etching the second layer to define a well over the first layer and the sensor pad of the sensor array; and
   etching to form an access through the first layer and to remove the third layer, the access exposing the sensor pad to the well.

7. The method of claim 6, wherein the first inorganic material comprises an oxide of silicon.

8. The method of claim 6, wherein the polymeric material comprises a polyimide.

9. The method of claim 6, wherein the second inorganic material comprises a low temperature oxide of silicon.

10. The method of claim 6, wherein etching to form the access includes etching with a fluorine-containing plasma.

* * * * *